(12) United States Patent
Bang et al.

(10) Patent No.: US 10,072,247 B2
(45) Date of Patent: Sep. 11, 2018

(54) COMPOSITION COMPRISING ISCHEMIC SERUM FOR PROMOTING ACTIVATION OF STEM CELL AND METHOD FOR PROMOTING ACTIVATION OF STEM CELL

(71) Applicant: Samsung Life Public Welfare Foundation, Yongsan-gu, Seoul (KR)

(72) Inventors: Oh Young Bang, Seoul (KR); Gyeong Joon Moon, Seongnam-si (KR); Yeon Hee Cho, Seoul (KR); Suk Jae Kim, Seoul (KR); Dong Hee Kim, Seoul (KR); Soo Kyung Ryoo, Seoul (KR); Ji Hyun Lee, Busan (KR); Ji Yoon Nam, Seoul (KR); Ji Hee Sung, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 14/433,495

(22) PCT Filed: Oct. 4, 2013

(86) PCT No.: PCT/KR2013/008904
§ 371 (c)(1),
(2) Date: Jul. 30, 2015

(87) PCT Pub. No.: WO2014/054917
PCT Pub. Date: Apr. 10, 2014

(65) Prior Publication Data
US 2015/0337264 A1    Nov. 26, 2015

(30) Foreign Application Priority Data

Oct. 5, 2012  (KR) .................. 10-2012-0110876

(51) Int. Cl.
| | | |
|---|---|---|
| *C12N 5/0775* | (2010.01) | |
| *A61K 35/16* | (2015.01) | |
| *A61K 35/28* | (2015.01) | |
| *A61K 35/12* | (2015.01) | |

(52) U.S. Cl.
CPC ............ *C12N 5/0663* (2013.01); *A61K 35/16* (2013.01); *A61K 35/28* (2013.01); *A61K 2035/124* (2013.01); *C12N 2500/84* (2013.01)

(58) Field of Classification Search
CPC .. C12N 5/0663; C12N 2500/84; A61K 35/25; A61K 35/16; A61K 2035/124
See application file for complete search history.

(56) References Cited

U.S. PATENT DOCUMENTS

| 7,978,638 B2 | 7/2011 | Kim et al. |
| 8,951,511 B2 | 2/2015 | Koh et al. |
| 2010/0119492 A1 | 5/2010 | Hans et al. |

FOREIGN PATENT DOCUMENTS

| KR | 10-2004-0062610 | 7/2004 |
| KR | 10-2011-0042468 | 4/2011 |
| KR | 10-2011-0097785 | 8/2011 |

OTHER PUBLICATIONS

Thompson et al. (1990). Serum Enzyme Levels During Intestinal Ischemia. Ann Surg, v211(3), p. 369-373.*
Chang et al. Role of Stromal Cell-Derived Factor-1α, Level and Value of Circulating Interleukin-10 and Endothelial Progenitor Cells in Patients With Acute Myocardial Infarction Undergoing Primary Coronary Angioplasty. Circ J (2009); v73, p. 1097-1104.*
Arakeylan et al. Serum Levels of the MCP-1 Chemokine in Patients With Ischemic Stroke and Myocardial Infarction Mediators of Inflammation (2005), v3, p. 175-179.*
Leone et al. Endogenous G-CSF and CD34+ cell mobilization after acute myocardial infarction. International Journal of Cardiology (2006), v111(2), p. 202-208.*
Gottlieb et al. Brain-derived neurotrophic factor blood levels in two models of transient brain ischemia in rats. Gen. Physiol. Biophys. (2013), v32, p. 139-142.*
Stanzani et al. Nerve Growth Factor and Transforming Growth Factor-P Serum Levels in Acute Stroke Patients. Cerebrovasc Dis (2001), v12(3), p. 240-244.*
Chen et al. Ischemic rat brain extracts induce human marrow stromal cell growth factor production. Journal of Neuroscience Research (2002), v69, p. 687-691.*
Honmou et al. Intravenous administration of auto serum-expanded autologous mesenchymal stem cells in stroke. Brain (2011), v134, p. 1790-1807.*
Yamasaki et al. Transient Increase of Cytokine-Induced Neutrophil Chemoattractant, a Member of the Interleukin-8 Family, in Ischemic Brain Areas After Focal Ischemia in Rats. Stroke (1995), v26(2), 13 page reprint.*
Slevin et al. Serial Measurement of Vascular Endothelial Growth Factor and Transforming Growth Factor-b1 in Serum of Patients With Acute Ischemic Stroke. Stroke (2000), v31, p. 1863-1870.*
Bang, et al. "Autologous Mesenchymal Stem Cell Transplantation in Stroke Patients," Annals of Neurology, 57(6):874-882 Jun. 2005.
Lee, et al. "A Long-term follow-up study of intravenous autologous mesenchymal stem cell transplantation in patients with ischemic stroke," Stem Cells, 28:1099-1106, 2010.
Zacharek, et al. "Comparison of Bone marrow stromal cells derived from stroke and normal rats for stroke treatment," Stroke, 41(3):524-530, Mar. 2010.
Qu, et al. "Neurotrophic and growth factor gene expression profiling of mouse bone marrow stromal cells induced by ischemic brain extracts," Neuropathology, Aug. 2007, 27(4):355-363.

(Continued)

*Primary Examiner* — Sean C. Barron
(74) *Attorney, Agent, or Firm* — McDonnell Boehnen Hulbert & Berghoff LLP

(57) ABSTRACT

The present invention relates to a composition comprising an ischemic serum for promoting the activation of a stem cell, to a method for promoting the activation of a stem cell and to a stem cell, the activation of which is promoted by the composition or the method. The ischemic serum according to the present invention may stimulate the stem cell to facilitate the secretion of a growth factor, improve survival rate, improve mobility to an injured part, improve proliferation rate and maintain characteristics of the stem cell, thus promoting an activation of the stem cell such that the stem cell becomes suitable for transplantation of the stem cell to a patient having a brain injury.

4 Claims, 14 Drawing Sheets

(56) References Cited

OTHER PUBLICATIONS

Van Velthoven, et al. "Mesenchymal stem cells as a treatment for neonatal ischemic brain damage," Pediatric Research, 71:474-481, Apr. 2012.
Kim, et al. "Intravenous trans plantation of mesenchymal stem cells preconditioned with early phase stroke serum: current evidence and study protocol for a randomized trail," Trials, 14(1): e317 , Oct. 2013.
International Search Report for PCT/KR2013/008904, dated Jan. 24, 2014.

* cited by examiner

[Fig.1]
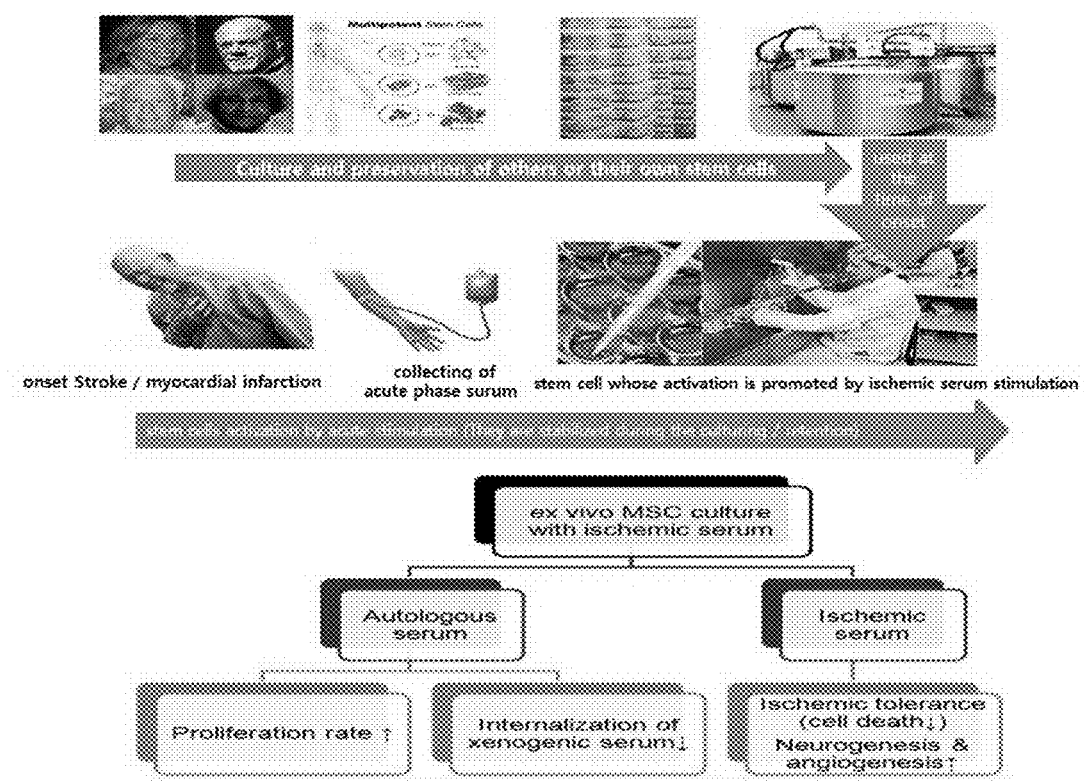

[Fig. 2a]
(A)
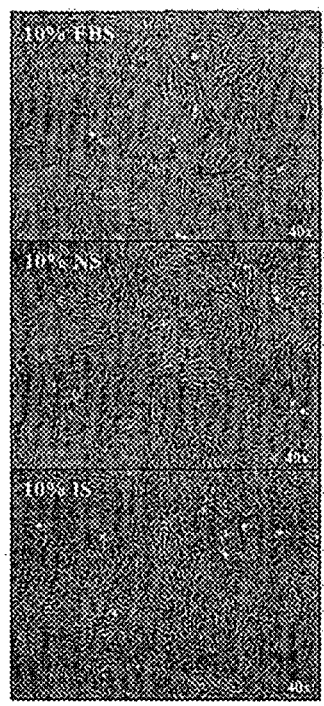
[Fig. 2b]
(B)
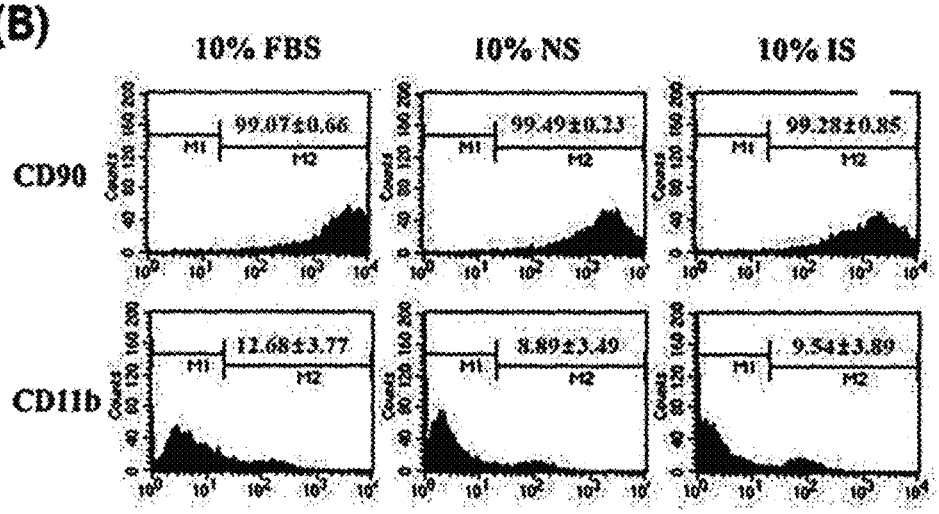

[Fig. 2c]
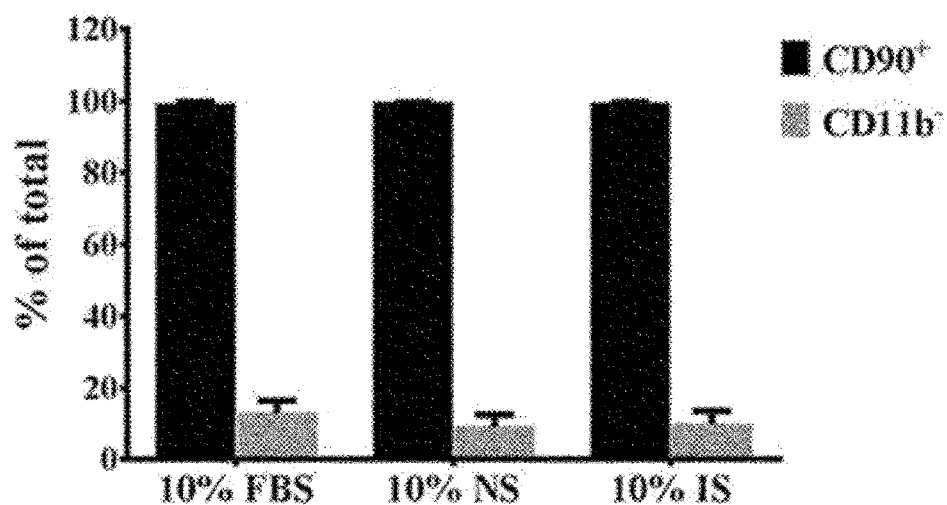
[Fig. 2d]
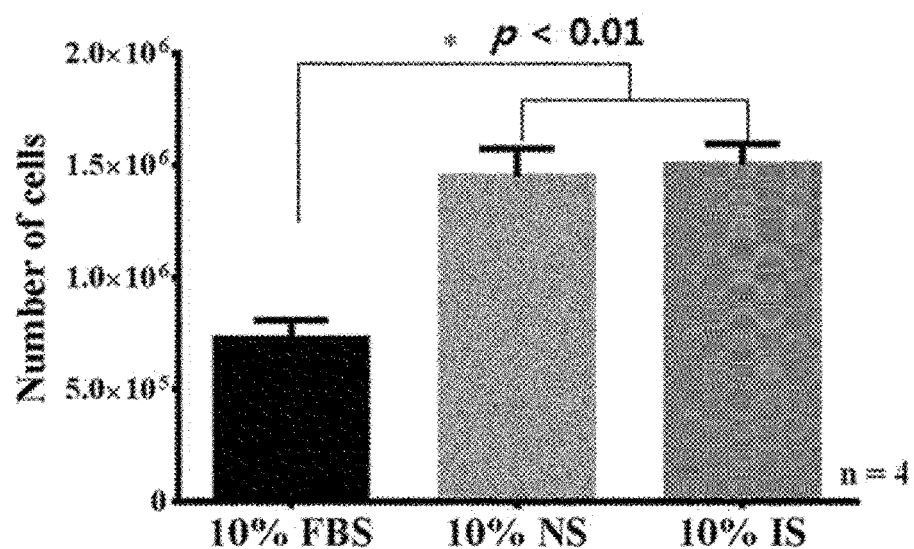

[Fig. 2e]
(E)
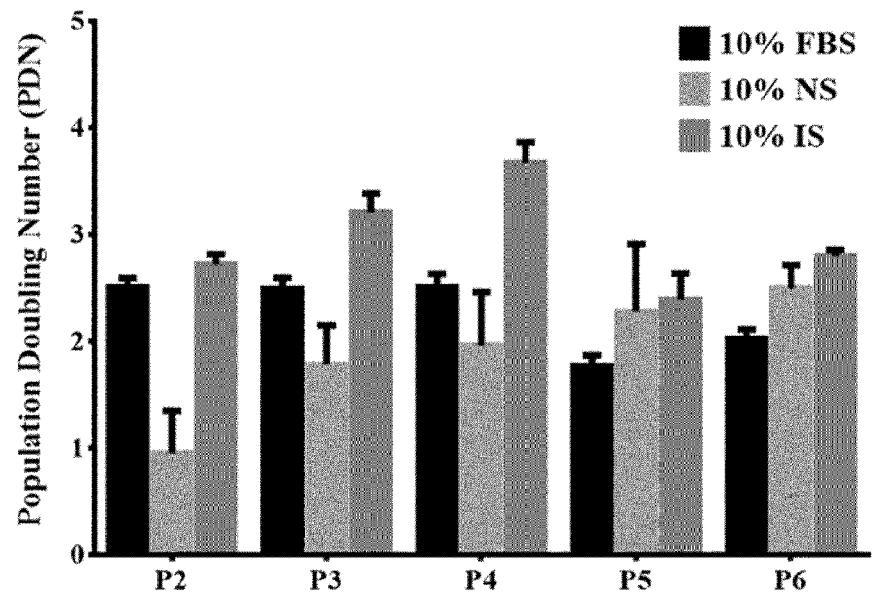
[Fig. 3a]
(A)
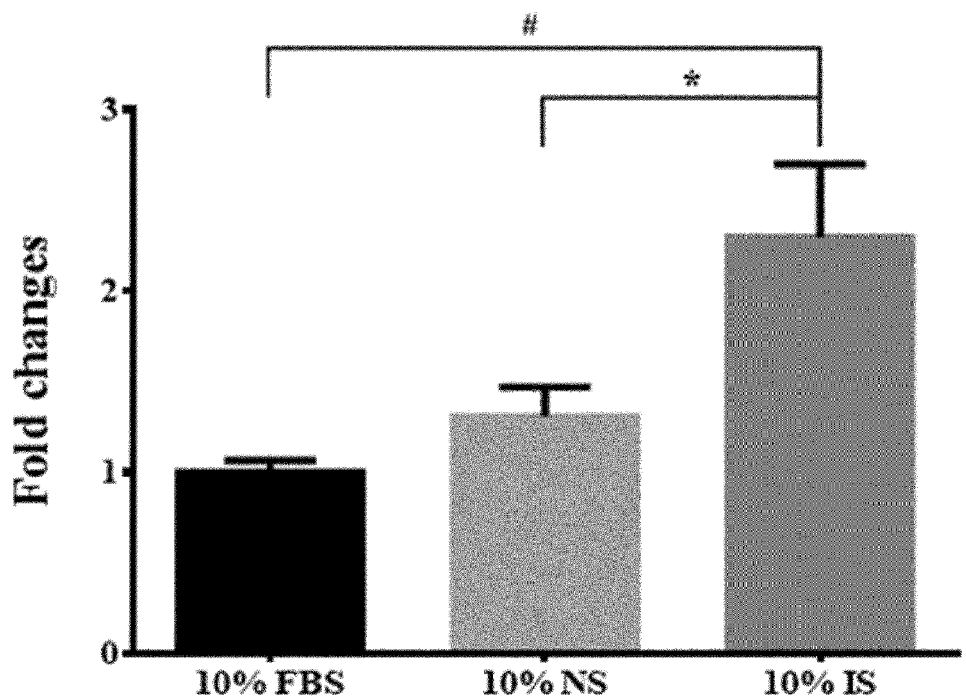

[Fig. 3b]
(B) GDNF
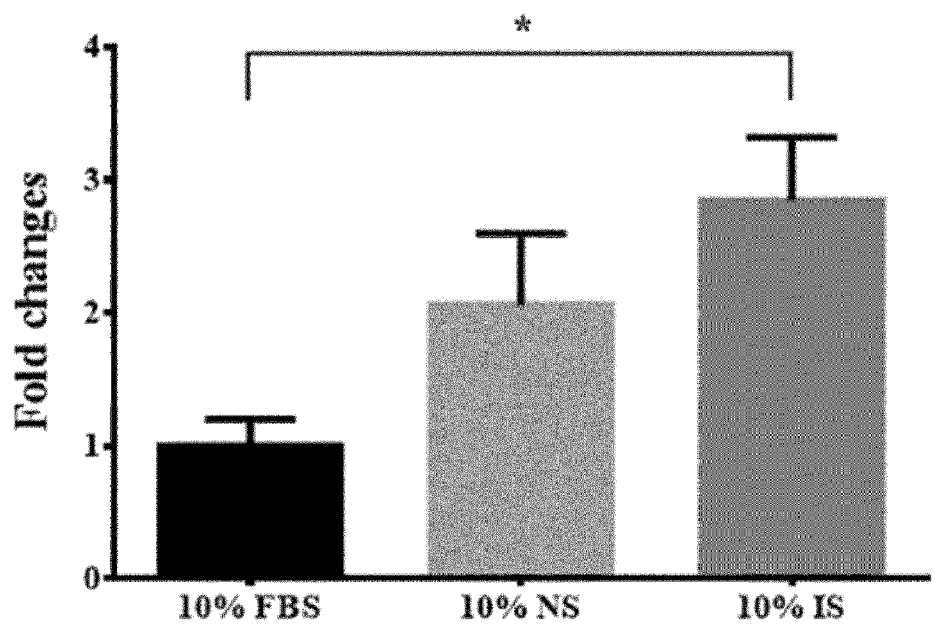
[Fig. 3c]
(C) HGF
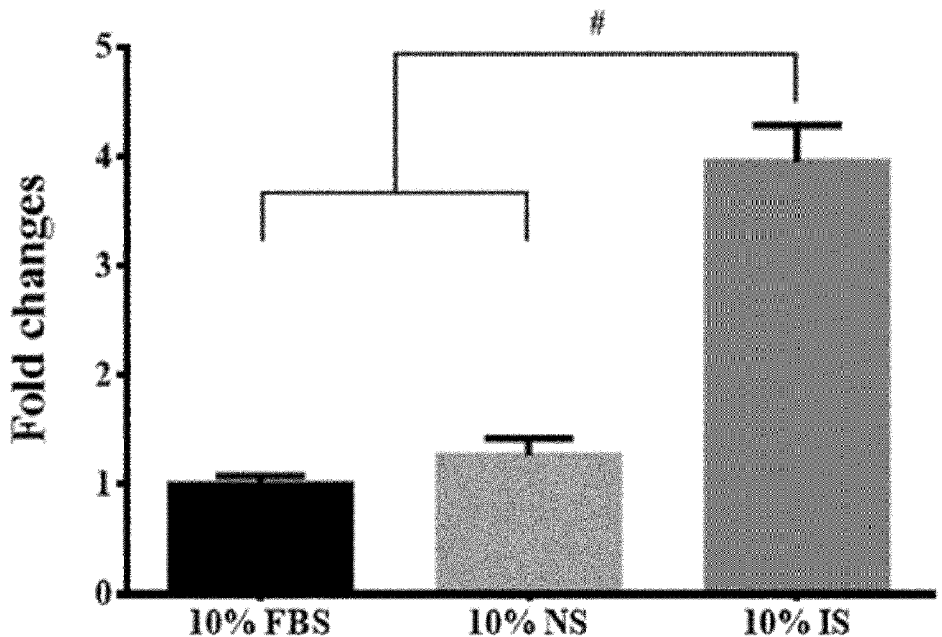

[Fig. 3d]
(D) bFGF
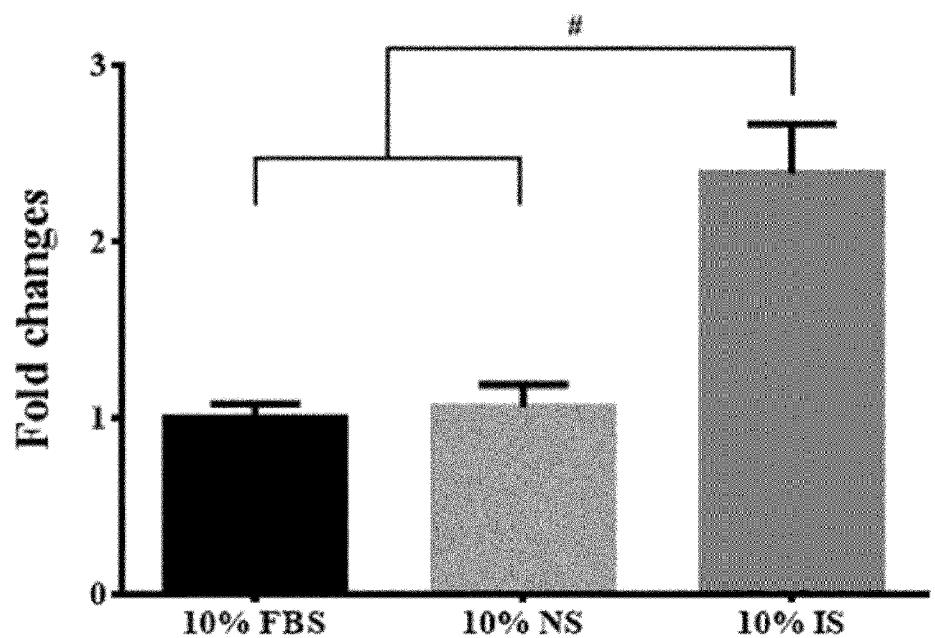
[Fig. 3e]
(E) BDNF
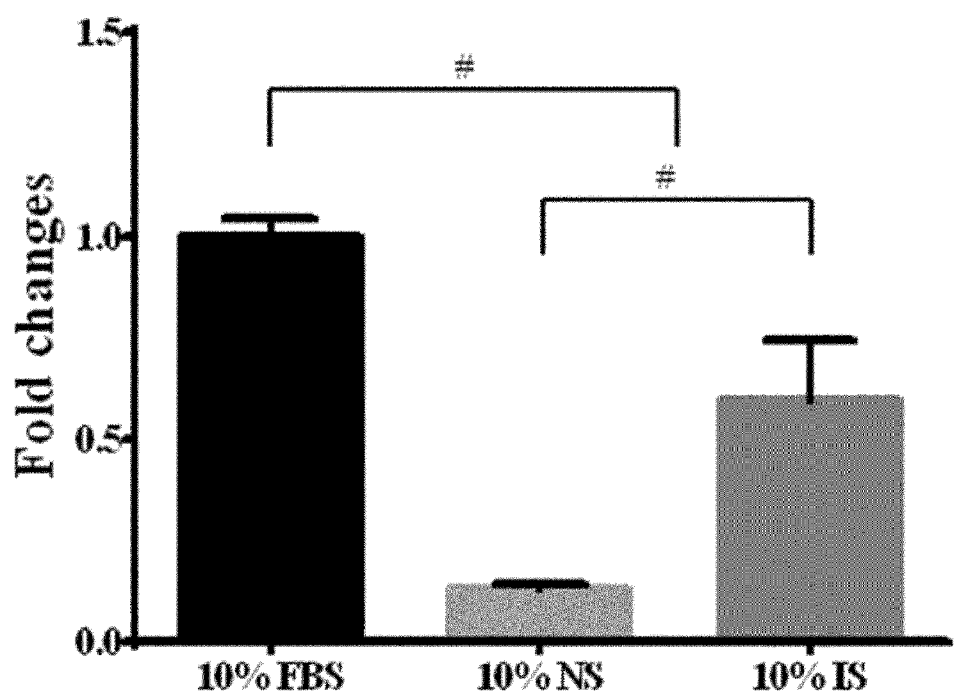

[Fig. 3f]
(F)
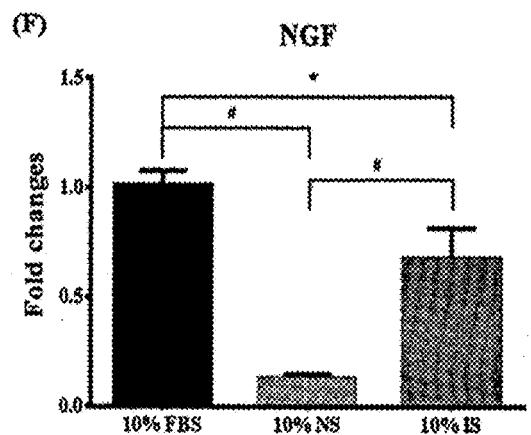
[Fig. 4a]
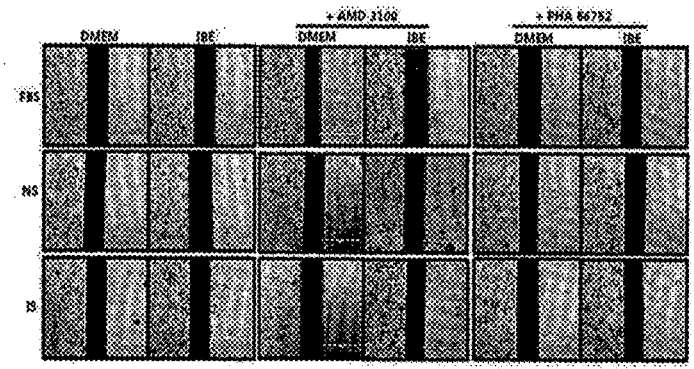
[Fig. 4b]
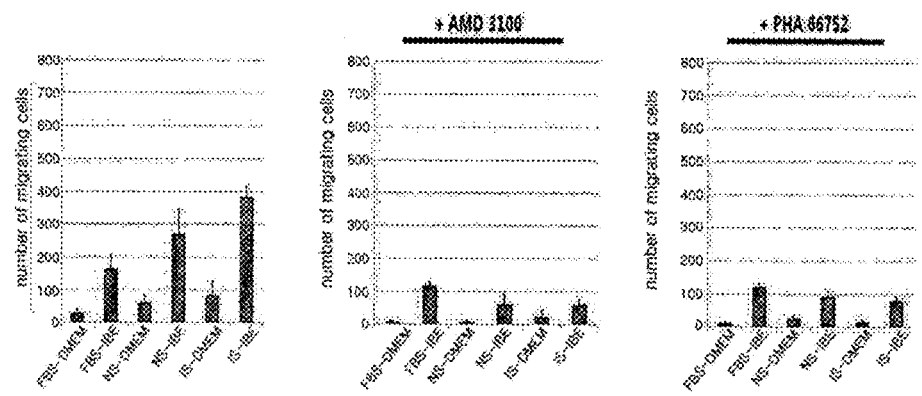

[Fig. 5]
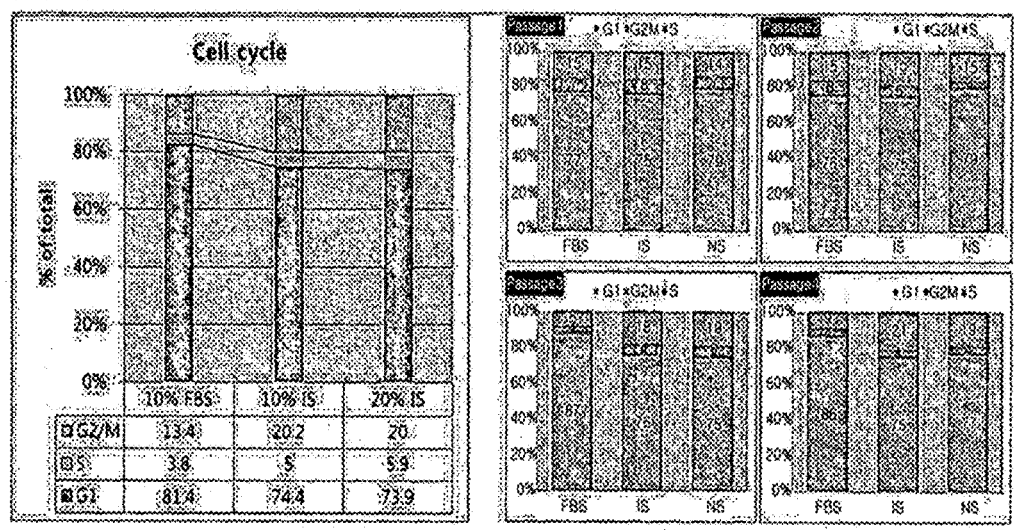
[Fig. 6a]
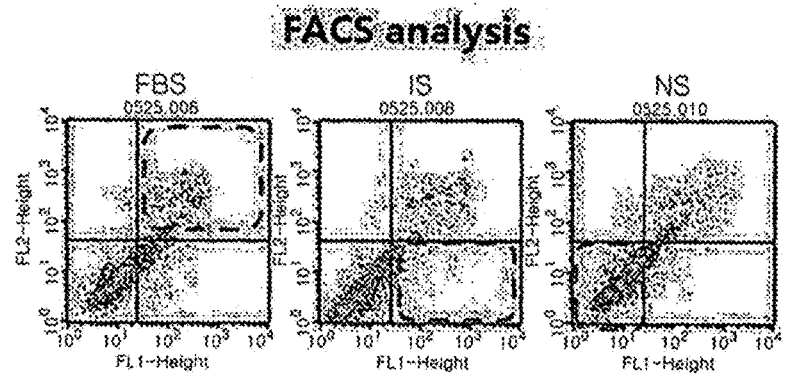
[Fig. 6b]
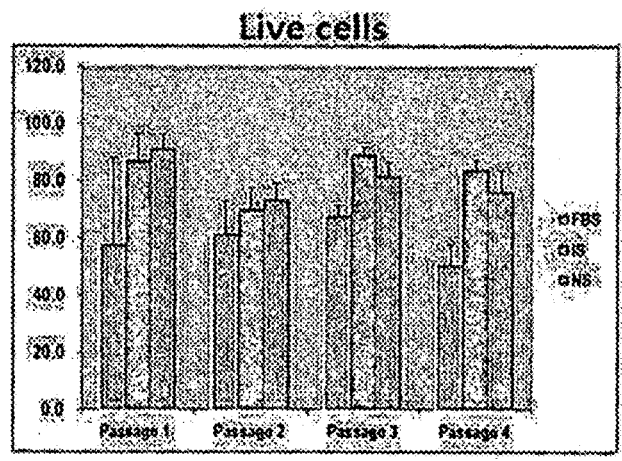

[Fig. 7]
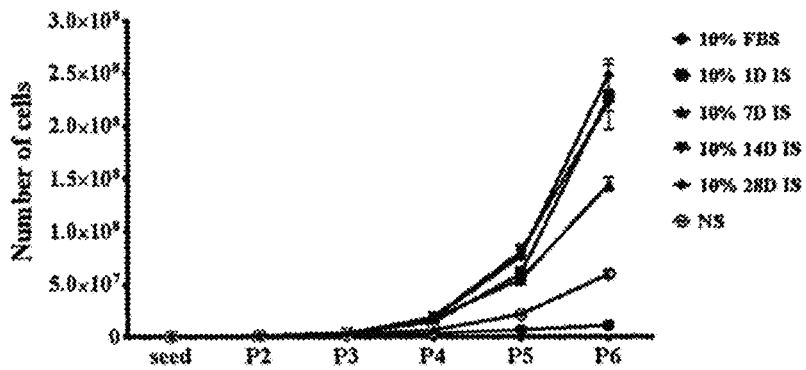
[Fig. 8]
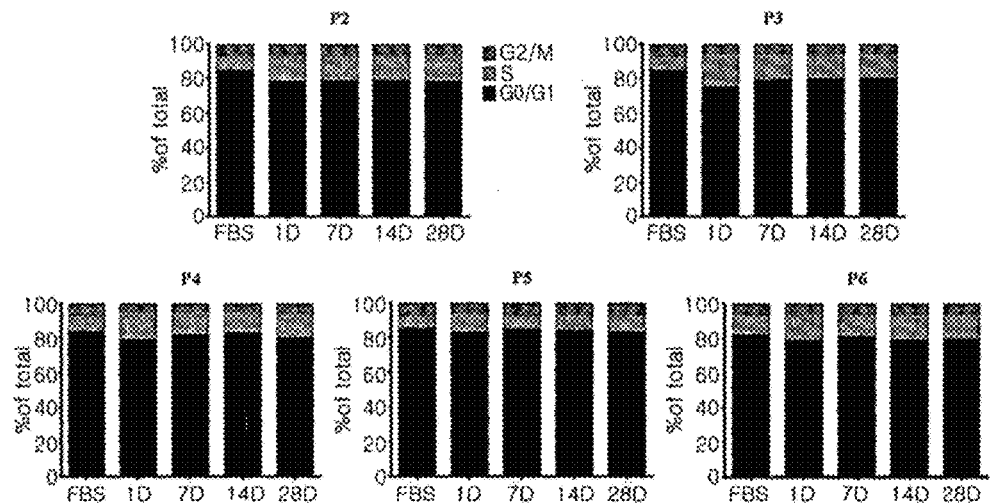
[Fig. 9]
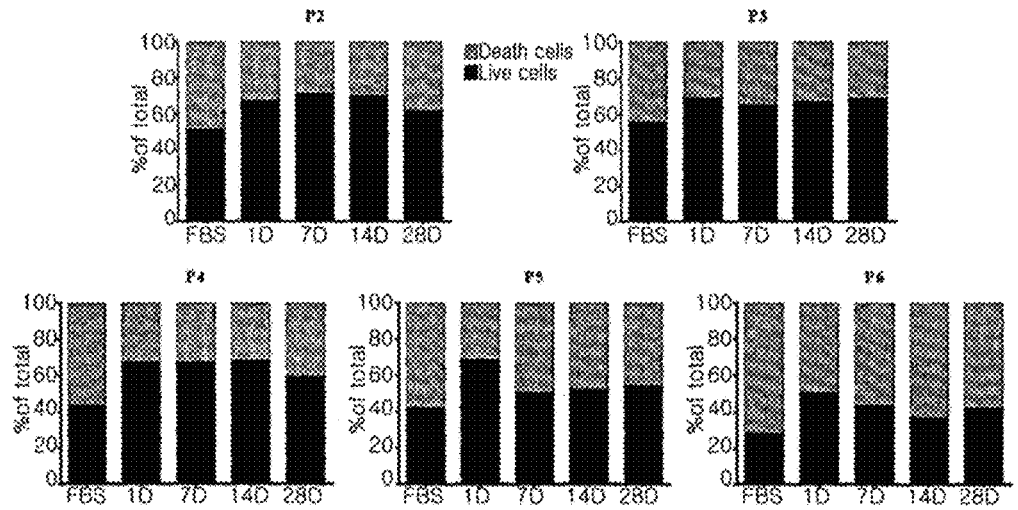

[Fig. 10a]
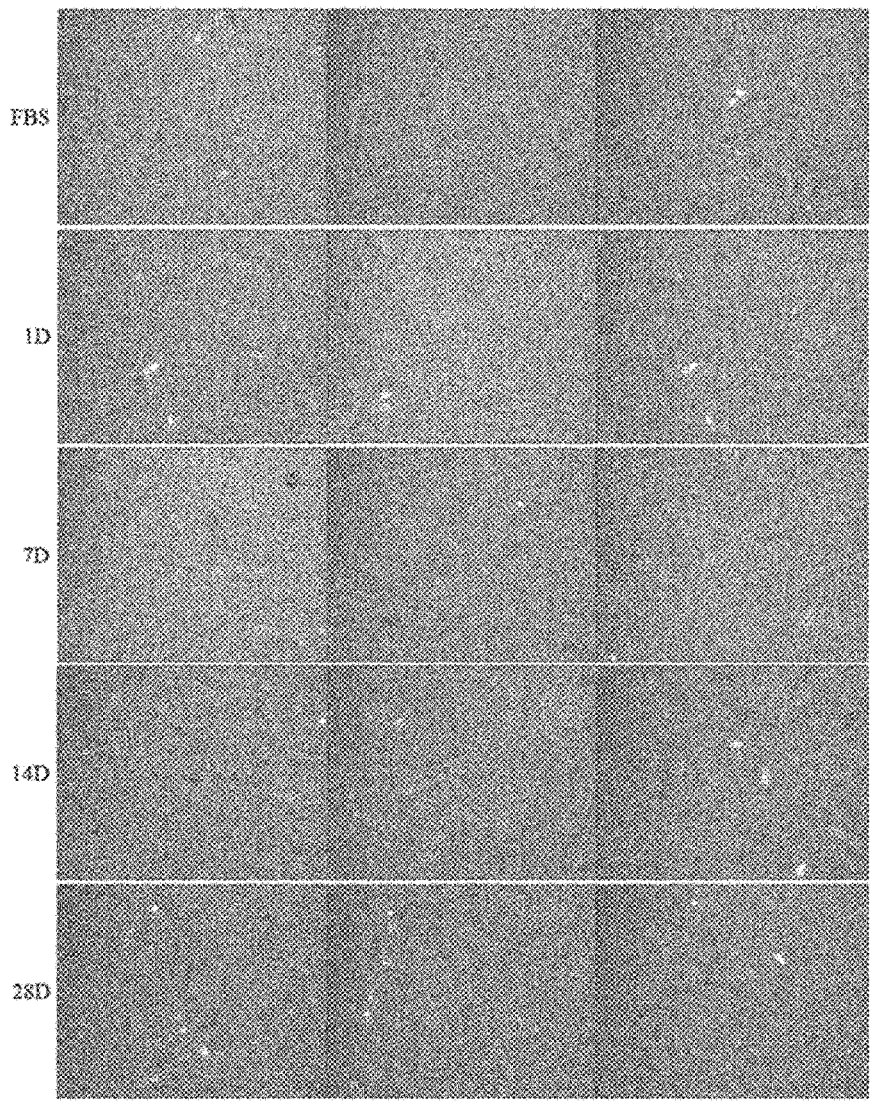

[Fig. 10b]
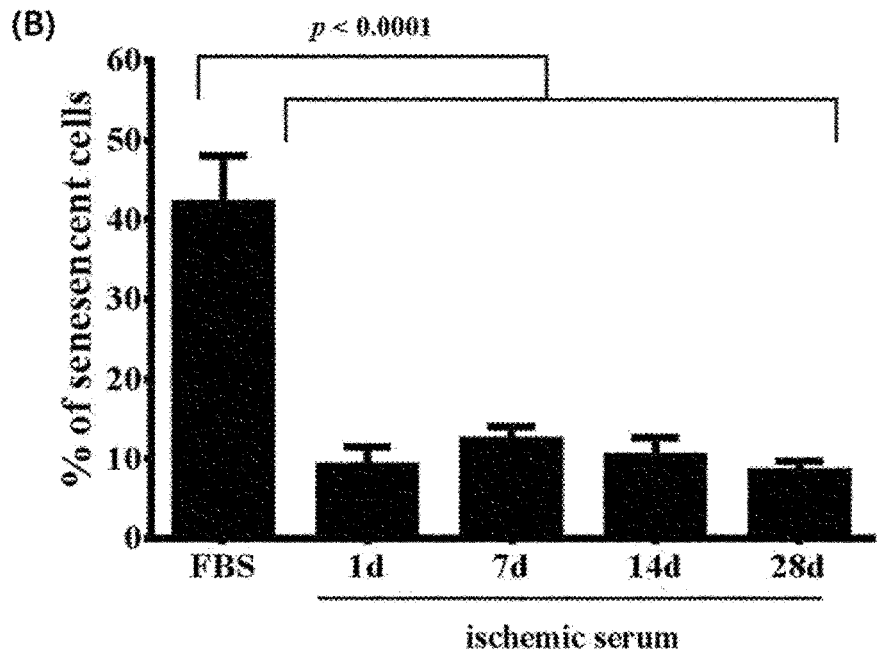
[Fig. 11a]
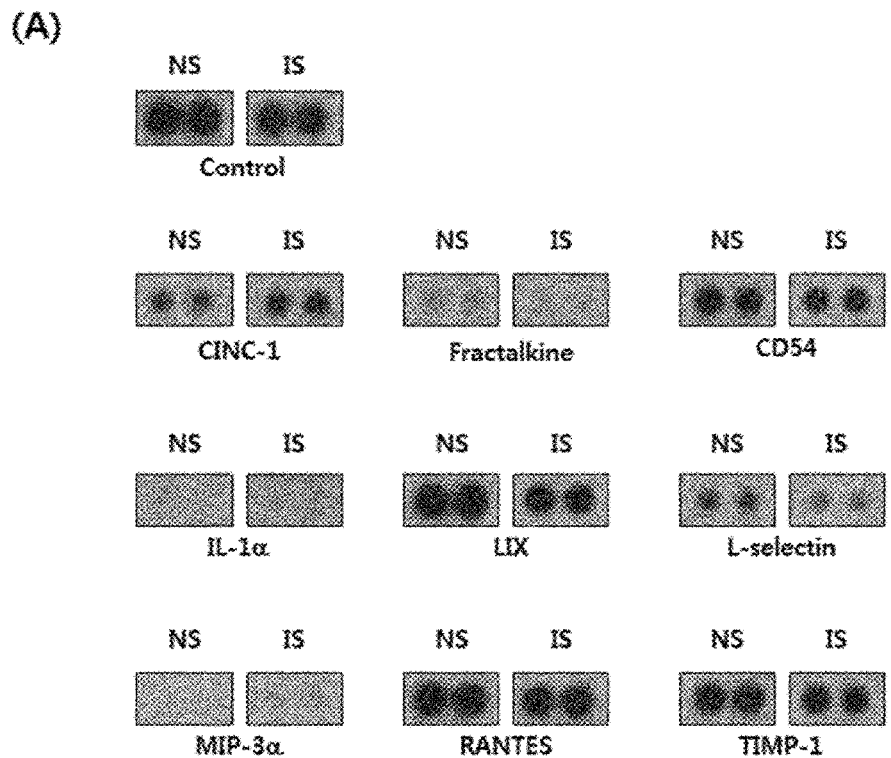

[Fig. 11b]
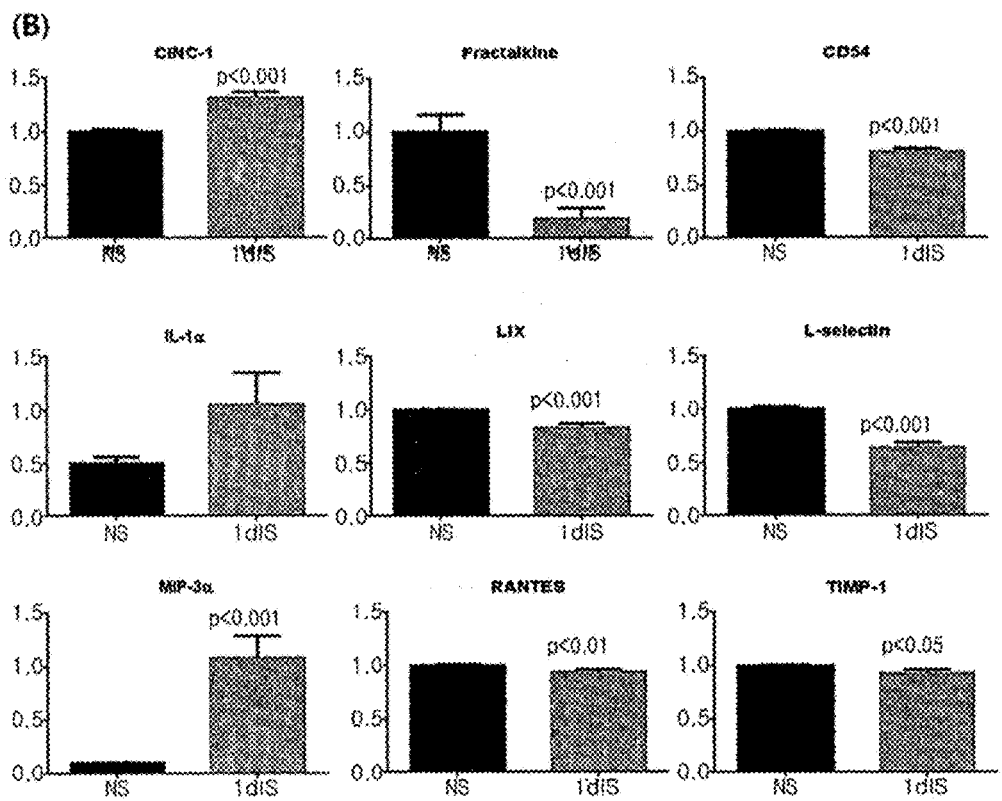
[Fig. 11c]
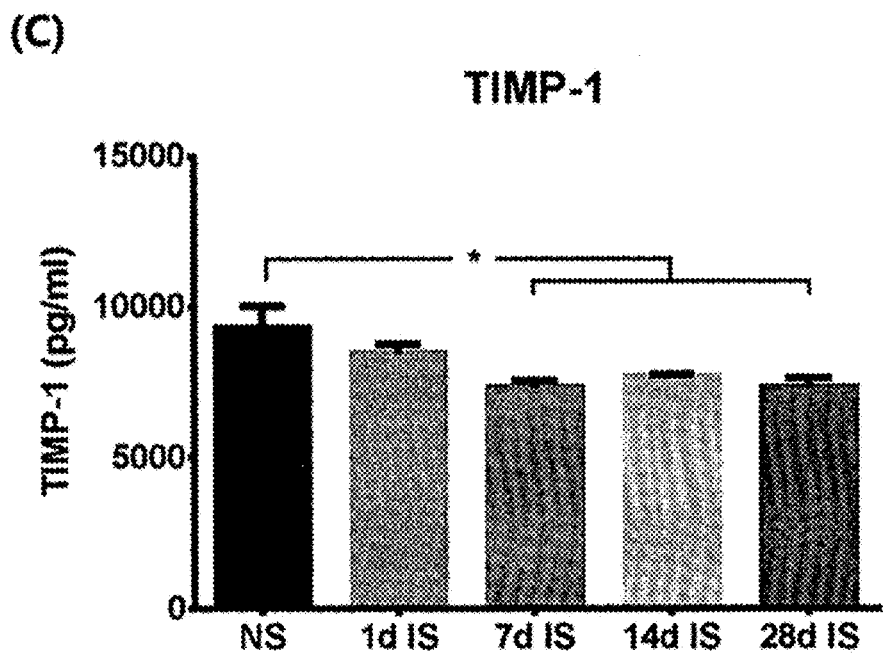

[Fig. 11d]
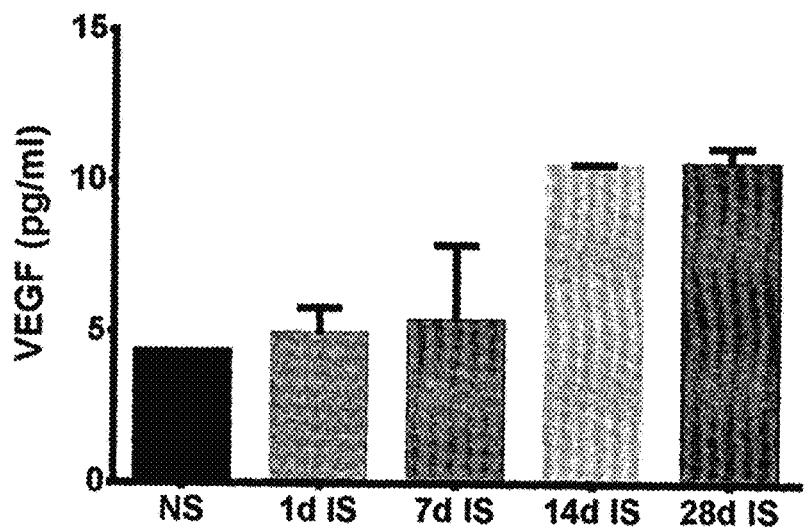
[Fig. 12a]
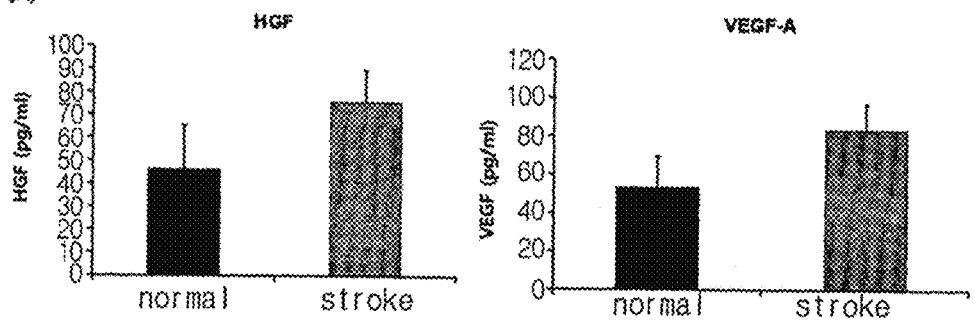
[Fig. 12b]
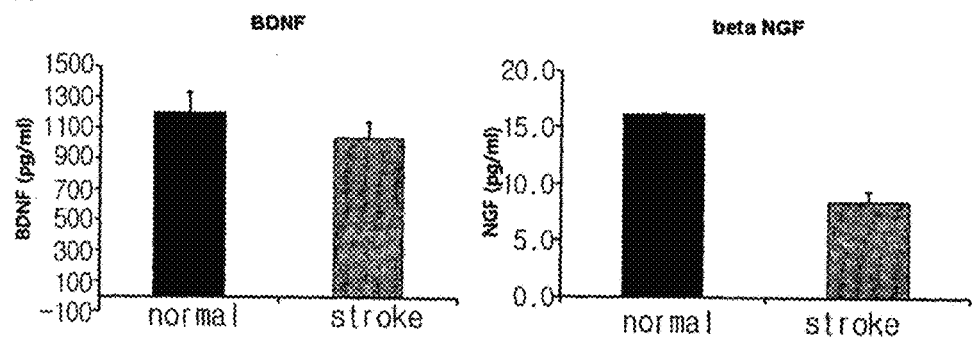

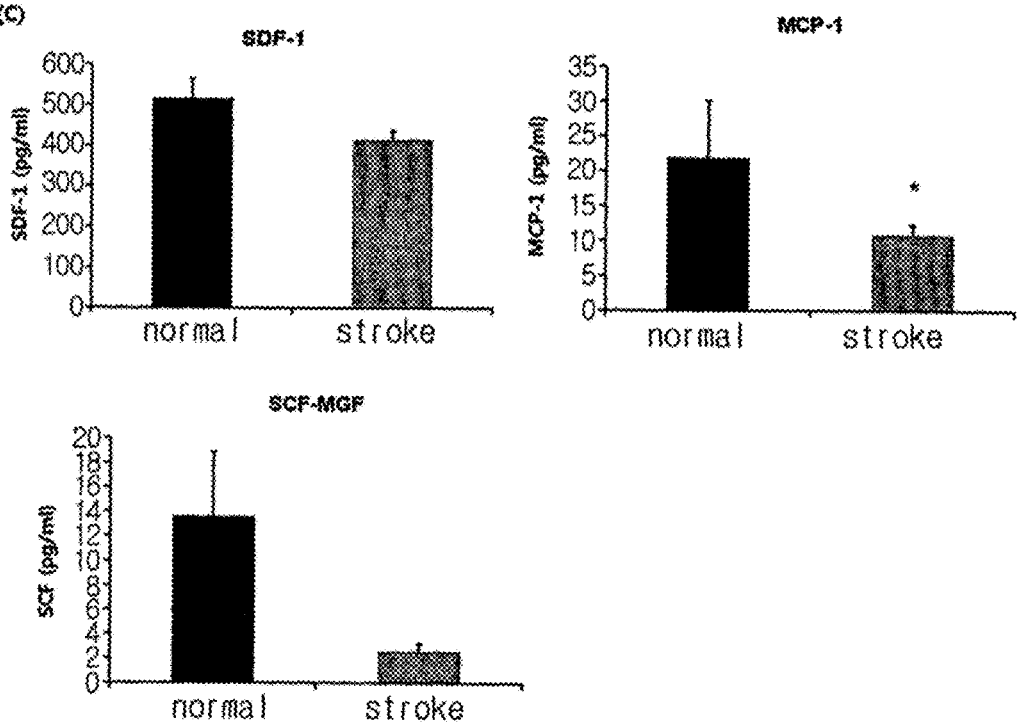

COMPOSITION COMPRISING ISCHEMIC SERUM FOR PROMOTING ACTIVATION OF STEM CELL AND METHOD FOR PROMOTING ACTIVATION OF STEM CELL

This application is a US national phase of International Application No. PCT/KR2013/008904 filed on Oct. 4, 2013, which claims priority to Korean Patent Application No. 10-2012-0110876 filed on Oct. 5, 2012, incorporated herein by reference in their entirety.

TECHNICAL FIELD

The present invention relates to a composition comprising ischemic serum for promoting the activation of stem cells and a method for promoting the activation of stem cells.

Moreover, the present invention relates to a stem cell whose activation is promoted by ischemic serum stimulation.

BACKGROUND ART

Biotechnology in the 21$^{st}$ century presents the possibility of new solutions to the food, environment, and health problems, with the ultimate goal of improving human welfare. In recent years, the therapy using stem cells has been considered as a new way to treat incurable diseases. Formerly, organ transplantation, gene therapy, etc., were presented for the treatment of incurable human diseases, but their efficient use has not been made due to immune rejection, short supply of organs, insufficient development of vectors, and insufficient knowledge of disease genes.

As an alternative to solve these problems, the interest in stem cells has grown, and it has been recognized that totipotent stem cells having the ability to form all organs by proliferation and differentiation can be applied to the treatment of most diseases as well as to the treatment of incurable diseases, including Parkinson's disease, various cancers, diabetes, spinal cord injuries, etc.

Stem cells refer to cells having not only self-replication ability but also the ability to differentiate into at least two cells, and embryonic stem cells, induced pluripotent stem cells, and adult stem cells have been most actively studied. Among others, in the case of embryonic stem cells and induced pluripotent stem cells, there are still limitations in their application to the human body due to ethical issues or stability issues such as tumorigenesis. The adult stem cells are advantageous in terms of stability, and thus clinical studies have been conducted in patients. However, among the adult stem cells, in the case of neural stem cells and cord blood cells, the autograft, which is the transplantation of their own cells, is not yet feasible, and thus it is necessary to transplant neural stem cells from other people. Bone marrow or fat-derived mesenchymal stem cells can be easily obtained from the human body and thus have been most actively studied in clinical trials.

With respect to cell therapy using mesenchymal stem cells, a long-term clinical research on cell therapy for isolation and proliferation of mesenchymal stem cells from their own bone marrow, followed by intravenous transplantation, has been reported (Bang O Y, Lee J S, Lee P H, Lee G. Autologous mesenchymal stem cell transplantation in stroke patients. Ann Neurol. 2005; 57:874-882) (Lee J S, Hong J M, Moon G J, Lee P H, Ahn Y H, Bang O Y. A long-term follow-up study of intravenous autologous mesenchymal stem cell transplantation in patients with ischemic stroke. Stem Cells. 2010; 28:1099-1106). However, even in the case of mesenchymal stem cells with these advantages, it takes more than 4 to 5 weeks to culture mesenchymal stem cells isolated from bone marrow to reach a sufficient concentration (about $1 \times 10^8$ cells) that can be used for cell therapy, which is problematic.

As such, the autograft is impossible depending on the types of stem cells, or even when autograft is feasible, it takes a long time to culture stem cells until a desired therapeutic effect is achieved, and thus research on allograft has been conducted. That is, the use of cells derived from a healthy person is much easier than the use of cells derived from a patient, and thus extensive research on cell therapy using allogeneic stem cells has recently been actively conducted.

However, even in the development of allogeneic therapies with the above-described advantages, the following problems have been reported:

(a) It has been reported that stem cells derived from a healthy person and stem cells from a patient (e.g., a stroke patient) have different characteristics. That is, it has been reported that stem cells derived from bone marrow of a stroke animal are excellent in functional recovery after stroke, compared to stem cells derived from bone marrow of a healthy animal (Zacharek A, Shehadah A, Chen J, Cui X, Roberts C, Lu M, Chopp M. Comparison of bone marrow stromal cells derived from stroke and normal rats for stroke treatment. Stroke. 2010; 41:524-530). Therefore, even during the allograft, it is necessary to activate stem cells to be suitable for transplantation by applying appropriate stimuli to stem cells, instead of simply transplanting stem cells from other people. Moreover, even in the case of stem cells derived from a patient, the characteristics of stem cells are likely to vary during culture in fetal bovine serum for a long time;

(b) After a predetermined time from transplantation of stem cells, the number of stem cells is significantly reduced, and this results from cell death that occurs when stem cells are in a toxic environment such as cerebral infarction and myocardial infarction. Therefore, in the stem cell therapy, it is important to improve the viability of stem cells to be transplanted such that stem cells can survive in this environment for a long time to maintain the therapeutic effect;

(c) The effect of cell therapy after the occurrence of acute injuries such as cerebral infarction and myocardial infarction is determined by how fast stem cells are transplanted. However, as mentioned above, even in the transplantation of autologous or allogeneic stem cells, it takes a long time to culture stem cells to a concentration suitable for cell therapy, which makes it impossible to transplant stem cells to a patient in need of treatment in a timely manner. Therefore, it is necessary to reduce the culture period by increasing the proliferation rate by applying appropriate stimuli to stem cells to be activated and further minimize the loss of conditioning that have been applied to stem cells at the time of acute injury during culture; and (d) Fetal bovine serum (FBS) is generally used for the culture of stem cells, but it has been reported that some fetal bovine serum is introduced into stem cells, causing the risk of zoonoses such as bovine spongiform encephalopathy.

As such, various limitations have been reported with the use of autologous or allogeneic stem cells in the stem cell therapy to treat brain injured patients, but a suitable method for inducing the activation of stem cells to overcome these limitations has not yet been reported. Therefore, in order to overcome the existing limitations of stem cell therapy, it is necessary to develop a method for activating stem cells to be suitable for stem cell therapy.

DISCLOSURE

Technical Problem

The present inventors have studied a method for applying appropriate stimuli to stem cells to maintain an activated state in the early stage of cerebral infarction, which is suitable for transplantation, and found that the stimulation of stem cells with ischemic serum promotes the activation of stem cells, which increases the secretion of growth factors from stem cells, increases the proliferation rate, and improves the viability, thereby completing the present invention.

An object of the present invention is to provide a composition for promoting the activation of stem cells, comprising ischemic serum as an active ingredient, and a method for promoting the activation of stem cells using the same.

Moreover, another object of the present invention is to provide an activated stem cell cultured in a medium containing ischemic serum.

Technical Solution

To achieve the above objects, the present invention provides a composition for promoting the activation of stem cells, comprising ischemic serum as an active ingredient, and a method for promoting the activation of stem cells.

Moreover, the present invention provides an activated stem cell cultured in a medium containing ischemic serum.

Furthermore, the present invention provides a pharmaceutical composition for the treatment of ischemic diseases, comprising a stem cell cultured in a medium containing ischemic serum as an active ingredient.

Advantageous Effects

The ischemic serum according to the present invention can stimulate stem cells to promote the activation of stem cells to be suitable for transplantation into brain injured patients so as to increase the secretion of growth factors, improve the viability, enhance the migration to injured sites, increase the proliferation rate, and maintain the characteristics of stem cells.

DESCRIPTION OF DRAWINGS

FIG. 1 is a schematic diagram showing the gist of the present invention which activates stem cells using ischemic serum that is an acute stimulus.

FIG. 2A shows images of stem cells cultured using FBS, normal serum, and ischemic serum, FIGS. 2B and 2C show stem cell phenotypes determined by flow cytometric analysis, and FIGS. 2D and 2E show the cell proliferation rate (FBS: fetal bovine serum-treated group; IS: ischemic serum-treated group; NS: normal serum-treated group).

FIGS. 3A to 3F show the gene expression of growth factors (VEGF, GDNF, HGF, bFGF) and stem cell differentiation factor (BDNF and NGF) of stem cells from mesenchymal stem cells cultured with ischemic serum or FBS, determined by real-time PCR (10% FBS: 10% fetal bovine serum-treated group; 10% IS: 10% ischemic serum-treated group; 10% NS: 10% normal serum-treated group).

FIGS. 4A and 4B show the promotion of migration of stem cells treated with ischemic serum to ischemic tissues and the change in migration of stem cells after treatment with inhibitors such as AMD3100 and PHA66752 (FBS: fetal bovine serum-treated group; IS: ischemic serum-treated group; NS: normal serum-treated group; IBE: ischemic brain extract-treated group).

FIG. 5 shows the changes in cell growth rate and cell cycle due to ischemic serum treatment.

FIGS. 6A to 6D show the change in viability of stem cells due to ischemic serum treatment determined under ischemic brain-like conditions (FBS: fetal bovine serum-treated group; IS: ischemic serum-treated group; NS: normal serum-treated group).

FIG. 7 shows the change in number of cells over time during culture of mesenchymal stem cells after treatment with ischemic sera obtained over time after inducing ischemia in a cerebral ischemia animal (P3: cultured to passage 3; P4: cultured to passage 4; FBS: fetal bovine serum-treated group; 1D IS: ischemic serum-treated group on the $1^{st}$ day after stroke; 7D IS: ischemic serum-treated group on the $7^{th}$ day after stroke; 14D IS: ischemic serum-treated group on the $14^{th}$ day after stroke; 28D IS: ischemic serum-treated group on the $28^{th}$ day after stroke).

FIG. 8 shows the change in cell cycle over time during culture of mesenchymal stem cells after treatment with ischemic sera obtained over time after inducing ischemia in a cerebral ischemia animal (P3: cultured to passage 3; P4: cultured to passage 4; FBS: fetal bovine serum-treated group; 1D IS: ischemic serum-treated group on the $1^{st}$ day after stroke; 7D IS: ischemic serum-treated group on the $7^{th}$ day after stroke; 14D IS: ischemic serum-treated group on the $14^{th}$ day after stroke; 28D IS: ischemic serum-treated group on the $28^{th}$ day after stroke).

FIG. 9 shows the viability of stem cells under ischemic brain-like conditions during culture of mesenchymal stem cells after treatment with ischemic sera obtained over time after inducing ischemia in a cerebral ischemia animal (P3: cultured to passage 3; P4: cultured to passage 4; FBS: fetal bovine serum-treated group; 1D IS: ischemic serum-treated group on the $1^{st}$ day after stroke; 7D IS: ischemic serum-treated group on the $7^{th}$ day after stroke; 14D IS: ischemic serum-treated group on the $14^{th}$ day after stroke; 28D IS: ischemic serum-treated group on the $28^{th}$ day after stroke).

FIGS. 10A and 10B show the degree of senescence in mesenchymal stem cells cultured from passage 2 after treatment with ischemic sera obtained over time after inducing ischemia in a cerebral ischemia animal, determined by beta-galactosidase staining at passage 6 (P3: cultured to passage 3; P4: cultured to passage 4; FBS: fetal bovine serum-treated group; 1D IS: ischemic serum-treated group on the $1^{st}$ day after stroke; 7D IS: ischemic serum-treated group on the $7^{th}$ day after stroke; 14D IS: ischemic serum-treated group on the $14^{th}$ day after stroke; 28D IS: ischemic serum-treated group on the $28^{th}$ day after stroke).

FIG. 11A shows the level of cytokine contained in ischemic serum obtained 1 day after inducing ischemia in a cerebral ischemia animal, observed in comparison with normal serum, FIG. 11B shows the results of cytokine antibody array performed on sera obtained from a normal rat and a stroke-induced rat, from which it can be seen that the levels of CINC-1, IL-1α, and MIP-3α in ischemic serum is higher than those in normal serum, but the levels of fractalkine, CD54, LIX, L-selectin, RANTES, and TIMP-1 are lower than those in normal serum (NS: normal serum; IS: ischemic serum), and FIGS. 11C and 11D show the levels of TIMP-1 and VEGF contained in ischemic serum obtained over time after inducing ischemia in a cerebral ischemia animal, from which it can be seen that the level of TIMP-1 in the ischemic serum obtained on the $1^{st}$ day tends to decrease compared to normal serum, and the level of TIMP-1 in the sera on the $7^{th}$, $14^{th}$, and $28^{th}$ days statistically significantly decreases, and the level of VEGF in the ischemic serum tends to increase compared to normal serum (1D IS: ischemic serum on the 1$^{st}$ day after stroke; 7D IS: ischemic serum on the 7$^{th}$ day after stroke; 14D IS: ischemic serum on the 14$^{th}$ day after stroke; 28D IS: ischemic serum on the 28$^{th}$ day after stroke).

FIGS. 12A to 12C show the levels of cytokine and growth factors contained in sera obtained from a stroke patient and a normal control group, determined by cytokine multiplex. The results of quantitative analysis indicate that the levels of growth factors such as VEGF and HGF are high in the serum of the stroke patient (FIG. 12A), the levels of BDNF and NGF are low (FIG. 12B), and the levels of chemokines such as MCP-1, SDF-1, and SCF are low in the serum of the stroke patient (FIG. 12C).

BEST MODE FOR CARRYING OUT THE INVENTION

The present invention provides a composition for promoting the activation of stem cells, comprising ischemic serum as an active ingredient.

The ischemic serum according to the present invention can stimulate stem cells to promote the activation of stem cells to be suitable for transplantation into brain injured patients so as to increase the secretion of growth factors, improve the viability, enhance the migration to injured sites, and increase the proliferation rate.

The ischemic serum refers to serum obtained from a patient with at least one disease selected from the group consisting of cerebral infarction, myocardial infarction, cerebral hemorrhage, neurotrauma, and spinal cord injury, and includes both autologous ischemic serum and allogeneic ischemic serum. The ischemic serum has properties different from those of normal serum, and thus the treatment of stem cells with the ischemic serum can promote the activation of stem cells.

When the ischemic serum is obtained from an acute cerebral infarction patient, it may be ischemic serum obtained from the patient within 1 to 90 days after the onset of cerebral infarction, preferably ischemic serum obtained within 1 to 30 days after the onset of cerebral infarction. During culture, the concentration of ischemic serum added may preferably be 5 to 20%, more preferably 10%.

The ischemic serum may comprise more inflammatory cytokines and cell growth factors than those in normal serum. The inflammatory cytokine may be cytokine-induced neutrophil chemoattractant-1 (CINC-1), interleukin-1α (IL-1α), or macrophage inflammatory protein 3α (MIP-3α), and the cell growth factor may be vascular endothelial growth factor (VEGF), glial cell-derived neurotrophic factor (GDNF), hepatocyte growth factor (HGF), or basic fibroblast growth factor (bFGF), but not limited thereto.

Moreover, the ischemic serum may comprise less cell differentiation factors and chemokines than those in normal serum. The chemokine may include stromal cell-derived factor-1 (SDF-1), monocyte chemoattractant protein-1 (MCP-1), or stem cell factor (SCF), and the cell differentiation factor may include brain derived neurotrophic factor (BDNF) or nerve growth factor (NGF), but not limited thereto.

Stem cells may be activated by exposure to active substances, and the activation of stem cells can increase the secretion of growth factors, improve the viability, enhance the migration to injured sites, increase the proliferation rate, and maintain the characteristics of stem cells and represents that the stem cells are to be suitable for transplantation. Activated stem cells can be directly transplanted into injured sites without having to be subjected to long-term culture. The activation of stem cells may be accompanied with changes in cell cycle and growth factor genes by the stimulation of active substances. Therefore, the promoted activation of stem cells refers to the induction and promotion of normally cultured stem cells to be suitable for transplantation into injured sites.

The stem cells may include adult stem cells, embryonic stem cells, mesenchymal stem cells, adipose stem cells, hematopoietic stem cells, cord blood stem cells, and induced pluripotent stem cells and may be allogeneic or autologous stem cells.

Moreover, the present invention provides a medium for promoting the activation of stem cells, containing ischemic serum as an active ingredient, and a method for promoting the activation of stem cells, comprising the step of culturing stem cells in the medium.

The medium for promoting the activation of stem cells is a medium that is generally used in the art and contains ischemic serum. Dulbecco's modified essential medium (DMEM) or neural progenitor cell basal medium (NPBM; Clonetics), which are generally used for cell culture, can be used as a preferred medium.

Moreover, the basic medium may be supplemented with basic fibroblast growth factor (bFGF) or epidermal growth factor (EGF) alone or in combination in a concentration of 1 ng/ml to 100 ng/ml, preferably 10 ng/ml.

The medium containing ischemic serum for promoting the activation of stem cells may be supplemented with ischemic serum in a basic medium, which can stimulate stem cells to be activated. More specifically, the stem cells cultured in the medium are to be suitable for transplantation so as to increase the secretion of growth factors, improve the viability, enhance the migration to injured sites, and increase the proliferation rate.

The ischemic serum contained in the medium for promoting the activation of stem cells may preferably be contained in a concentration of 5 to 20%, more preferably 10%.

The culture for the activation of stem cells in a medium for promoting the activation of stem cells, containing ischemic serum as an active ingredient, may be performed at a temperature 33 to 38° C., preferably 37° C., for 24 hours.

There are no particular restrictions in other culture conditions, and the stem cells may be suspended or attached to a culture dish. The culture dish may include, for example, a chamber glass, non-coating dish, etc. which are widely used in the art.

Moreover, the present invention provides an activated stem cell cultured in a medium containing ischemic serum.

The activated stem cell comprises characteristic of increased the secretion of growth factors, improved the viability, enhanced the migration to injured sites, increased the proliferation rate, and maintained stem cells characteristics.

The growth factors refer to proteins that have important functions to regulate the proliferation, growth, maintenance, and survival of stem cells and may include, but not limited to, vascular endothelial growth factor (VEGF), glial cell-derived neurotrophic factor (GDNF), neurotrophin-3 (NT-3), neurotrophin-4 (NT-4), epidermal growth factor (EGF), basic fibroblast growth factor (bFGF), and ciliary neurotrophic factor (CNTF). The growth factors may preferably be VEGF, GDNF, HGF, or bFGF, which regulate the proliferation, growth, maintenance, and survival of stem cells, among the growth factors produced from stem cells stimulated during the culture of the present invention.

The injury refers to an injury caused by ischemia.

The increase in proliferation rate refers to an increase in cell proliferation rate, and the cell proliferation rate refers to the rate at which the number of cells is increased by self-renewal of stem cells.

Moreover, the present invention provides a pharmaceutical composition comprising the activated stem cell as an active ingredient for the prevention or treatment of ischemic diseases.

The ischemic serum according to the present invention can stimulate stem cells to promote the activation of stem cells to be suitable for transplantation into brain injured patients so as to increase the secretion of growth factors, improve the viability, enhance the migration to injured sites, increase the proliferation rate, and maintain the characteristics of stem cells. Therefore, the ischemic serum of the present invention can be effectively used for the prevention or treatment of ischemic diseases.

The ischemic diseases may include ischemic brain disease, ischemic heart disease, and ischemic peripheral vascular disease. The mechanisms of ischemic brain disease, ischemic heart disease, and ischemic peripheral vascular disease are very similar, and thus when the ischemic serum according to the present invention is effective in the treatment of ischemic brain diseases, it may have the same or similar effect on ischemic heart disease and ischemic peripheral vascular disease. The ischemic brain disease may include thrombosis, embolism, transient ischemic attack, cerebral infarction, cerebral hemorrhage, subarachnoid hemorrhage, white matter disorder, and lacunar infarction, and the ischemic heart disease may include myocardial infarction and angina.

The stem cells may be directly used for transplantation and may be transplanted as a composition supplemented with various agents or a composition in which genes are introduced so as to improve therapeutic efficiency.

In the preparation of the composition of the present invention, for example, it is possible to: (1) add a substance that improves the proliferation rate of cells of the present invention or that promotes the differentiation into neural cells, or introduce a gene that has these effects; (2) add a substance that improves the viability of cells of the present invention in injured neural tissues, or introduce a gene that has the same effect; (3) add a substance that inhibits adverse influences from injured neural tissues to the cells of the present invention, or introduce a gene that has the same effect; (4) add a substance that prolongs the life span of donor cells, or introduce a gene that has the same effect; (5) add a substance that regulates the cell cycle, or introduce a gene that has the same effect; (6) add a substance that is used to suppress the immune reaction, or introduce a gene that has the same effect; (7) add a substance that activates the energy metabolism, or introduce a gene that has the same effect; (8) add a substance that promotes the migration activity of donor cells in host tissues, or introduce a gene that has the same effect; (9) add a substance that improves blood flow, or introduce a gene that has the same effect (including induction of angiogenesis); and (10) add a substance that has a certain therapeutic effect on host brain nerves (with diseases to be treated including, for example, thrombosis, embolism, transient ischemic attack, cerebral infarction, cerebral hemorrhage, subarachnoid hemorrhage, white matter disorder, and lacunar infarction) or introduce a gene that has the same effect. However, the present invention is not limited to these examples.

The administration method of the stem cell according to the present invention is not particularly limited and, includes, for example, topical administration, intravenous administration, intraarterial administration, and intra-cerebrospinal administration (for example, lumbar puncture and intraventricular administration).

More specifically, the transplantation of cells into patients can be administered via any route as long as it can induce migration to disease sites. For example, the cell transplantation can be achieved by filling a syringe with cells to be transplanted, the cells being suspended in artificial cerebrospinal fluid, physiological saline, etc., exposing injured neural tissue by operation, and directly injecting the cells into the injured site with an injection needle. A method of loading stem cells into a vehicle provided with a means for directing the stem cells towards the lesion site can be contemplated. Therefore, the activated stem cells of the present invention can be administered via various routes such as topical administration (including buccal, sublingual, transdermal, and intraocular administration), parenteral administration (including subcutaneous, intradermal, intramuscular, instillation, intravenous, intraarterial, intraarticular, and intra-cerebrospinal administration), or percutaneous administration, preferably administered parenterally, most preferably directly into diseased sites. The stem cells of the present invention can effectively migrate into injured sits, particularly ischemic injuries due to their high migration activity.

Moreover, the injection into the cerebrospinal fluid may also be effective. In this case, the cells can be injected by typical lumbar puncture, and thus is preferable, since the patient is treated with only topical anesthesia and without operation in a sickroom. Furthermore, intraarterial injection and intravenous injection can also be effective.

Therefore, the transplantation can be practiced by the same procedure as typical blood transfusion. Such methods are preferable to those transplantation methods since the method can be used in a sickroom.

The pharmaceutical composition of the present invention can be used as a cell therapeutic agent, and the term "cell therapeutic agent" refers to a drug used for the purpose of treatment, diagnosis, and prevention, which contains a cell or tissue prepared through isolation from man, culture and specific operation (as provided by the US FDA). Specifically, it refers to a drug used for the purpose of treatment, diagnosis and prevention through a series of behaviors of in vitro multiplying and sorting living autologous, allogeneic and xenogeneic cells or changing the biological characteristics of cells by other means for the purpose of recovering the functions of cells and tissues.

Moreover, the pharmaceutical composition of the present invention may further comprise pharmaceutically acceptable carriers, excipients, and diluents for administration, in addition to the above-described active ingredient. Examples of carriers, excipients, and diluents may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, and mineral oil.

The pharmaceutical composition of the present invention may be prepared into various parenteral formulations. A representative example of the parenteral formulation may preferably be an isotonic aqueous solution or suspension as an injectable formulation. The injectable formulation may be prepared by a method known in the art using a suitable dispersant or wetting agent and a suspending agent by any method known in the art. For example, the respective ingredients may be dissolved in a saline or buffer solution to be formulated into an injectable formulation.

Formulations for parenteral administration may include sterile solutions, non-aqueous solvents, suspensions, emulsions, freeze-dried formulations, and suppositories. Propylene glycol, polyethylene glycol, vegetable oil such as olive oil, and injectable ester such as ethyl oleate, etc. can be used as the non-aqueous solvents and suspensions. Witepsol, macrogol, Tween 61, cacao oil, laurin oil, glycerogelatin, etc. can be used as suppository bases.

The effective dosage of the pharmaceutical composition of the present invention may vary depending on the age, gender, and weight of a patient, but can be administered to an subject after being suspended in a suitable diluent at a concentration of $1 \times 10^3$ to $5 \times 10^6$ cells/ml. The diluent is used to protect and maintain cells and to allow the cells to be easily transplanted into a target tissue. Examples of the diluent may include buffered solutions such as physiological saline, phosphate buffer solution, HBSS, etc., blood plasma, cerebrospinal fluid, blood components, etc.

For the treatment of ischemic brain diseases, the composition of the present invention can be used alone or in combination with surgical operation, chemical therapy, radiotherapy, hormone therapy, drug therapy, and methods using biological response modifiers.

MODE FOR INVENTION

In the following, the present invention will be described in detail with reference Preparation Examples and Examples. However, the following Preparation Examples and Examples are provided only to illustrate the present invention, and the present invention is not limited by the following Preparation Examples and Examples.

Example 1: Collection and Culture of Bone Marrow-Derived Stem Cells

Bone marrow was collected from a rat and diluted with phosphate buffer solution (PBS) at a ratio of 1:1 then mesenchymal stem cells were obtained by centrifugation and culture. The obtained mesenchymal stem cells were cultured in 5% $CO_2$ at 37° C., and then cells cultured to passages 2 to 5 (P2-5) were used in the Examples. The experiments were performed with the approval of the Experimental Animal Committee.

Example 2: Stimulation of Stem Cells with Ischemic Serum $3 \times 10^5$ bone marrow-derived mesenchymal stem cells obtained in Example 1 were cultured in 35 mm culture dishes and divided into treatment groups and a control group. The control group was cultured in DMEM supplemented with 10% FBS, and the normal serum-treated group and the ischemic serum-treated group were cultured in media supplemented with 10% normal serum (NS) and 10% ischemic serum (IS), respectively, for 24 hours (treated once and cultured to passages 4-5) or cultured without FBS from the initial culture. The cells were treated with ischemic serum continuously up to passages 4-5, and the culture was performed for 3 days per passage. The experiments were repeatedly performed three times for each group. The ischemic serum used in the ischemic serum-treated group was obtained from a rat 1 day after inducing middle cerebral artery infarction in the rat. The ischemic serum was used to induce acute stimulation in stable stem cells, and it was determined whether the stem cells were activated to be suitable for transplantation into patients by the acute stimulation. The process of activating stem cells using ischemic serum according to the present invention is shown in FIG. 1.

2.1 Changes in Phenotype and Cell Number of Stem Cells Treated with Ischemic Serum The phenotypes of stem cells cultured with FBS, normal serum, and ischemic serum were compared using flow cytometric analysis, and the change in cell number before and after the pretreatment was quantified.

The results are shown in FIG. 2.

As shown in FIG. 2A, it was observed that there was no difference in phenotype between the normal serum-treated group, the ischemic serum-treated group, and the control group. Moreover, as shown in FIGS. 2B and 2C, the stem cells were negative for CD11b expressed on leukocytes, but positive for CD90, a stem cell marker, from which it was found that the ischemic serum treatment did not influence the phenotype of stem cells. Increased number of cells was observed in the normal serum or ischemic serum-treated group after single culture, compared to the FBS-treated group, which is shown in the graph of FIG. 2D. The results of continuous culture for 2 to 6 passages indicate that the proliferation rate of stem cells cultured in a medium supplemented with ischemic serum is higher than that of stem cells cultured in a medium supplemented with normal serum or FBS, which is shown in the graph of FIG. 2E.

2.2 Determination of Expression of Growth Factors in Stem Cells Treated with Ischemic Serum It was determined whether the treatment of mesenchymal stem cells with ischemic serum could increase the gene expression of growth factors using the normal serum and ischemic serum-treated groups (10% NS and 10% IS) and the control group treated with FBS. In the respective treatment groups and the control group, the changes in gene expression of BDNF and NGF involved in the cell differentiation, and growth factor, such as VEGF, GDNF, HGF, bFGFF involved in the cell growth were determined by real-time PCR.

The results are shown in FIG. 3.

As shown in FIG. 3A, the level of VEGF was increased in the ischemic serum-treated group, compared to the FBS or normal serum-treated group. Moreover, the level of GDNF was not significantly different between the ischemic serum-treated group and the normal serum-treated group, but increased compared to the control group treated with FBS as shown in FIG. 3B. Furthermore, the gene expression of HGF and bFGF was increased in the ischemic serum-treated group compared to the FBS or normal serum-treated group as shown in FIGS. 3C and 3D.

On the contrary, the gene expression of BDNF and NGF that induce the differentiation of stem cells into neurons was lower in the normal serum and ischemic serum-treated groups than in the control group treated with FBS.

In summary, the expression of growth factors involved in the cell proliferation and growth increases, and the expression of growth factors that induce the differentiation decreases, from which it can be seen that the ischemic serum treatment can regulate the expression of growth factors in stem cells.

2.3 Determination of Migration Activity of Stem Cells Treated with Ischemic Serum The migration of stem cells is an important factor in the stem cell transplantation therapy, and thus the increase in migration of stem cells treated with ischemic serum to ischemic tissues was determined. The stem cells pretreated with ischemic serum and the stem cells without the ischemic serum treatment were cultured on chamber glass slides, and the number of stem cells migrating through agar gel containing ischemic brain extract for 48 hours was measured. Moreover, in order to inhibit SDF-1 and HGF that induce the migration of stem cells, the stem cells were treated with AMD3100, a chemokine SDF-1 antagonist, or PHA66752, an HGF receptor c-Met inhibitor, and the inhibition of the migration of stem cells was determined.

The results are shown in FIG. 4.

As shown in FIGS. 4A and 4B, compared to the stem cells without the ischemic serum pretreatment, the migration of stem cells activated by the ischemic serum pretreatment was increased and partially inhibited by the treatment with AMD3100 and PHA66752. These results indicate that the migration of stem cells is increased by the ischemic serum pretreatment, and various factors other than SDF-1 and HGF are involved in the migration of stem cells. Consequently, when stem cells are cultured with the ischemic serum pretreatment, the ability of stem cells to migrate to injured sites is improved, and thus it can be seen that the stem cells can selectively migrate to injured sites such as cerebral infarction.

2.4 Determination of Change in Cell Cycle Due to Ischemic Serum Treatment

Cells treated with trypsin were centrifuged at 1,300 rpm for 3 minutes to form pellets, and the pellets were resuspended in 1 ml of 90% ethanol and cultured at 4° C. overnight. The ethanol was removed by centrifugation at 1,500 rpm for 5 minutes, and the pellets were resuspended in 500 µl of PBS containing 0.1% triton X-100 and 20 µg/ml RNaseA. The resulting cells were cultured at 37° C. for 30 minutes and treated with 50 µg/ml of PI, and then the change in cell cycle due to the ischemic serum treatment was determined.

The results are shown in FIG. 5.

As shown in FIG. 5, it was found that the cells in S and G2/M phases were increased in the cells cultured with ischemic serum, compared to the cells cultured with FBS. Moreover, it was found that the cells in S and G2/M phases were increased after the single treatment with 10% and 20% ischemic sera (for 3 days), compared to those in 10% FBS culture. Moreover, it was found that when the cells were subcultured with 10% ischemic serum, the ratio of cells in S and G2/M phases was similar to that of 10% FBS culture at passage 1, but the ratio of cells in S and G2/M phases was increased by passages 2, 3 to 4, compared to that of 10% FBS culture.

2.5 Analysis of Viability of Stem Cells Due to Ischemic Serum Treatment

In order to determine whether stem cells stimulated with ischemic serum have resistance under ischemic conditions to increase the viability, the cell viabilities of the group treated with ischemic serum under ischemic brain-like conditions, the FBS-treated group, and the normal serum-treated group were compared and analyzed. Cells were subcultured with ischemic serum and treated with 20% ischemic brain extract to be cultured under ischemic brain-like conditions. Cells were treated with trypsin after 24 hours and centrifuged in 5% FBS-PBS at 1,300 rpm for 3 minutes to form pellets, and the pellets were resuspended in 150 µl of 1× binding buffer. Then, 10 µl of Annexin V-FITC and 10 µl of 50 µg/ml PI were added, reacted at room temperature for 15 minutes, and mixed with 350 µl of 1× binding buffer, followed by analysis.

The results are shown in FIG. 6.

As shown in FIGS. 6A to 6D, when stem cells were cultured under the stimulation of ischemic serum, the number of dead cells under ischemic brain-like conditions significantly decreased, compared to the cells cultured with FBS, and the number of survived cells increased. This indicates that when stem cells are treated with ischemic serum, the resistance to ischemia is increased, and when the stem cells are transplanted into ischemic sites, the viability of stem cells can be increased.

2.6 Determination of Change in Cell Number Due to Ischemic Serum Treatment for Each Period after Ischemia Ischemic sera were obtained from a cerebral ischemia animal 1 day, 7 days, 14 days, and 28 days after inducing ischemia, cells were cultured from passage 2 to passage 6 in media supplemented with the ischemic sera, and the number of cells for each passage was measured on a microscope.

The results are shown in FIG. 7.

As shown in FIG. 7, when stem cells were cultured in a medium supplemented with ischemic sera obtained 1 day, 7 days, 14 days, and 28 days after inducing ischemia, the number of cells obtainable was increased with increasing passages.

2.7 Determination of Change in Cell Cycle Due to Ischemic Serum Treatment for Each Period after Ischemia Ischemic sera were obtained from a cerebral ischemia animal 1 day, 7 days, 14 days, and 28 days after inducing ischemia, cells cultured from passage 2 to passage 6 in media supplemented with the ischemic sera were treated with trypsin, centrifuged at 1,300 rpm for 3 minutes to form pellets, and the pellets were resuspended in 1 ml of 90% ethanol and cultured at 4° C. overnight. The ethanol was removed by centrifugation at 1,500 rpm for 5 minutes, and the pellets were resuspended in 500 µl of PBS containing 0.1% triton X-100 and 20 µg/ml RNaseA. The resulting cells were cultured at 37° C. for 30 minutes and treated with 50 µg/ml of PI, and then the change in cell cycle for each passage due to the ischemic serum treatment was determined.

The results were shown in FIG. 8.

As shown in FIG. 8, it was found that the number of cells in S and G2/M phases, the gene replication and cell division stages, was increased in the group cultured with the ischemic serum on the $1^{st}$ day for 2 to 6 passages, compared to the control group cultured with FBS. Moreover, it was found that the number of cells was increased in the groups cultured with ischemic sera on the $7^{th}$, $14^{th}$, and $28^{th}$ days for 2 to 4 passages, compared to the control group cultured with FBS.

2.8 Analysis of Viability of Stem Cells Due to Ischemic Serum Treatment for Each Period after Ischemia In order to determine whether stem cells cultured with ischemic serum for each period after ischemia have resistance under ischemic conditions to increase the viability, the cell viabilities of the groups treated with ischemic serum for each period under ischemic brain-like conditions and the FBS-treated group were compared and analyzed. Specifically, cells were subcultured with ischemic sera and treated with 20% ischemic brain extract to be cultured under ischemic brain-like conditions. Cells were treated with trypsin after 24 hours and centrifuged in 5% FBS-PBS at 1,300 rpm for 3 minutes to form pellets, and the pellets were resuspended in 150 µl of 1× binding buffer. Then, 10 µl of Annexin V-FITC and 10 µl of 50 µg/ml PI were added, reacted at room temperature for 15 minutes, and mixed with 350 µl of 1× binding buffer, followed by analysis.

The results are shown in FIG. 9.

As shown in FIG. 9, when stem cells were cultured with ischemic sera on the $1^{st}$, $7^{th}$, $14^{th}$, and $28^{th}$ days, the number of dead cells under ischemic brain-like conditions was significantly reduced, compared to the cells cultured with FBS, and the number of survived cells increased. Moreover, it was found that even when the subculture was repeated, the viability of stem cells cultured with ischemic serum under ischemic brain-like conditions was higher than that of stem cells cultured with FBS. This indicates that when stem cells are treated with ischemic serum, the resistance to ischemia is increased, and when the stem cells are transplanted into ischemic sites, the viability of stem cells can be increased.

2.9 Analysis of Senescence in Stem Cells Due to Ischemic Serum Treatment for Each Period after Ischemia In order to determine the effect of the ischemic serum culture on the senescence in stem cells, stem cells cultured with ischemic serum and FBS at passage 2 were stained with beta-galactosidase at passage 6, and compared and analyzed. Specifically, cells cultured with ischemic serum and FBS at passage 6 were fixed with 4% paraformaldehyde, treated with a mixture of 930 μl of 1× staining solution, 10 μl of staining supplement A, 10 μl of staining supplement B, 50 μl of 20 mg/ml X-gal solution (Cell Signaling products), and reacted 37° C. for 24 hours, followed by observation.

The results are shown in FIG. 10.

As shown in FIG. 10A, it was observed under microscope that the number of cells positive for beta-galactosidase staining in the stem cells cultured only with FBS was greater than that of the stem cells cultured with the ischemic sera obtained 1 day, 7 days, 14 days, and 28 days after ischemia. The number of cells positive for beta-galactosidase staining among the whole cells was measured, and the ratio is shown in the graph of FIG. 10B, from which it can be seen that the ischemic serum culture can delay the senescence in stem cells.

Example 3: Analysis of Cytokines and Cell Growth Factors of Ischemic Serum

The levels of cytokines and growth factors contained in the ischemic sera and normal serum used in Examples 1 and 2 were analyzed using a rat cytokine antibody array (R&D System) and ELISA. Moreover, the levels of cytokines and growth factors contained in sera of a stroke patient and a normal control were analyzed using a human cytokine multiplex (BIO-RAD). The experiments were repeatedly performed three times for each group.

3.1 Analysis of Cytokines and Growth Factors in Ischemic Serum of Cerebral Ischemia Animal The levels of cytokines and growth factors contained in the ischemic serum and normal serum obtained 1 day after inducing ischemia were analyzed using a rat cytokine antibody array (R&D System) and ELISA.

Specifically, a membrane coated with 29 types of different antibodies including cytokines and growth factors was incubated in a blocking buffer for 1 hour, and sera were reacted with detection antibodies for 1 hour. The resulting samples were added to the membrane and reacted at 4° C. for 12 hours. After the reaction, the membrane was washed with a washing solution three times and then reacted with streptavidin-HRP for 30 minutes. After the reaction, the membrane was washed with a washing solution three times and then developed into a film, and the results were analyzed.

The results are shown in FIG. 11.

As shown in FIG. 11A, it was found that 9 types of proteins such as CINC-1, fractalkine, CD54, IL-1alpha, LIX, L-selectin, MIP-3alpha, RANTES, and TIMP-1, among a total of 29 types of proteins, were developed into a film.

The respective spots developed into the film were normalized to control spots, followed by quantitative analysis, and the results are shown in FIG. 11B.

As shown in FIG. 11B, it was found that the levels of CINC-1, IL-1, and MIP-3 were high in ischemic serum, and the levels of Fractalkine, CD54, LIX, L-selectin, RANTES, TIMP-1 were low.

Moreover, the change in the levels of VEGF and TIMP-1 over time after ischemia was determined by ELISA, and the results are shown in FIGS. 11C and 11D.

As shown in FIGS. 11C and 11D, it was found that the level of TIMP-1 in the serum obtained on the $1^{st}$ day tended to decrease, and the level of TIMP-1 in the sera on the $7^{th}$, $14^{th}$, and $28^{th}$ days statistically significantly decreased (FIG. 11C). Moreover, the level of VEGF tended to increase over time after ischemia (FIG. 11D).

Consequently, it can be seen that the levels of inflammatory cytokines and growth factors that can activate stem cells are high in ischemic serum, and the level of cell adhesion molecules that can inhibit the cell division and growth is low.

3.2 Analysis of Cytokines and Growth Factors in Ischemic Serum of Stroke Patient Ischemic serum was obtained from a patient within 7 weeks after the onset of stroke and compared with normal serum to analyze the levels of cytokines and growth factors contained in the sera using a human cytokine multiplex (BIO-RAD).

Specifically, a standard sample was mixed with 250 μl of standard buffer, vortexed, and cultured on ice for 5 minutes. Then, the sample was transferred to a standard vial, vortexed, and cultured for 5 minutes. In order to dilute the prepared standard sample 4 times, each 150 μl of standard buffer was added to tubes 2-8, and 200 μl of standard buffer was added to tube 1. Then, each 50 μl was transferred from tube 1 to tube 2 and from tube 2 to tube 3 to be serially diluted. 150 μl of reading buffer was added to a filter plate and cultured for 5 minutes such that the filter was completely wet, and then the buffer was removed by vacuum filtration. Then, premixed antibody beads were vortexed for 30 seconds, and 50 μl was added to each well, and then the buffer was removed by vacuum filtration. The beads were washed with 150 μl of washing buffer, which was removed by vacuum, and each 25 μl of sample and standard sample was added to each well, sealed, and cultured on a plate shaker at 700 rpm for 60 minutes under room temperature conditions. After 60 minutes, the solution was removed by vacuum, and then the beads were washed with 150 μl of washing buffer three times. 25 μl of detection antibody was added, sealed, cultured with stirring at 700 rpm for 30 minutes, and then washed three times. 50 μl of streptavidin-PE (SAPE) solution was added to each well, cultured with stirring at 700 rpm for 30 minutes, and then washed three times. Then, 120 μl of reading buffer was added to each well, cultured with stirring at 700 rpm for 5 minutes, and then read on a Luminex instrument.

The results are shown in FIG. 12.

As shown in FIG. 12, the levels of growth factors such as HGF, VEGF, BDNF, and HGF and the levels of chemokines such as SDF-1, MCP-1, and SCF were different between the serum of the stroke patient and the normal serum. It was found that the levels of HGF and VEGF that can promote the growth and self-renewal of stem cells were high in the serum of the stroke patient (FIG. 12A), but the levels of BDNF and NGF that can induce the differentiation of stem cells into neurons were lower (FIG. 12B). Moreover, it was found that the levels of chemokines such as MCP-1, SDF-1, and SCF to which stem cells exhibit positive chemotaxis were lower in the serum of the stroke patient than the normal serum (FIG. 12C). This indicates that the levels of substances that regulate the activity of stem cells are different between the serum of the stroke patient and the normal serum.

Preparation Example 1: Preparation of Pharmaceutical Formulations 1.1 Preparation of Injections Stem cells cultured in a medium supplemented with ischemic serum: $5 \times 10^6$ cells/ml
Mannitol: 180 mg
Sterile distilled water for injection: 2974 mg
$Na_2HPO_4 \cdot H_2O$: 26 mg Injections are prepared with the above ingredients per ampoule (2 ml) by a typical preparation method of injections.

The invention claimed is:

1. A method for promoting the activation of mesenchymal stem cells, comprising the step of treating mesenchymal stem cells obtained from normal subjects with allogenic ischemic serum obtained from a patient with cerebral infarction,
   wherein the activation of mesenchymal stem cells comprises increased gene expression of growth factors, decreased gene expression of brain derived neurotrophic factor (BDNF) and nerve growth factor (NGF); and
   wherein the growth factors comprise endothelial growth factor (VEGF), glial cell-derived neurotrophic factor (GDNF), hepatocyte growth factor (HGF), and basic fibroblast growth factor (bFGF).

2. The method of claim 1, wherein the ischemic serum is obtained from a patient within 1 to 90 days after the onset of cerebral infarction.

3. The method of claim 1 wherein the treating of mesenchymal stem cells comprises culturing mesenchymal stem cells in a medium containing ischemic serum.

4. The method of claim 3, wherein the ischemic serum is contained in a concentration of 5 to 20%.

* * * * *